United States Patent
Kumagai et al.

(10) Patent No.: US 12,043,822 B2
(45) Date of Patent: Jul. 23, 2024

(54) APPARATUS FOR TREATING BIOLOGICAL MATERIAL

(71) Applicant: YAMAHA HATSUDOKI KABUSHIKI KAISHA, Iwata (JP)

(72) Inventors: Takahiko Kumagai, Shizuoka (JP); Saburo Ito, Shizuoka (JP); Kumi Akita, Shizuoka (JP)

(73) Assignee: YAMAHA HATSUDOKI KABUSHIKI KAISHA, Iwata (JP)

( * ) Notice: Subject to any disclaimer, the term of this patent is extended or adjusted under 35 U.S.C. 154(b) by 1031 days.

(21) Appl. No.: 16/965,188

(22) PCT Filed: Dec. 11, 2018

(86) PCT No.: PCT/JP2018/045562
§ 371 (c)(1),
(2) Date: Jul. 27, 2020

(87) PCT Pub. No.: WO2019/146291
PCT Pub. Date: Aug. 1, 2019

(65) Prior Publication Data
US 2021/0062132 A1    Mar. 4, 2021

(30) Foreign Application Priority Data

Jan. 29, 2018    (JP) ................................. 2018-012340

(51) Int. Cl.
*C12M 1/12*    (2006.01)
*C12M 1/00*    (2006.01)
(Continued)

(52) U.S. Cl.
CPC ............ *C12M 25/06* (2013.01); *C12M 23/22* (2013.01); *C12M 23/48* (2013.01); *C12M 33/06* (2013.01)

(58) Field of Classification Search
None
See application file for complete search history.

(56) References Cited

U.S. PATENT DOCUMENTS

2010/0097893 A1 *  4/2010  Ooi ........................ C12M 23/10
                                                        367/99
2012/0114219 A1    5/2012  Nakagawa et al.
(Continued)

FOREIGN PATENT DOCUMENTS

CN      105814188 A  *  7/2016  ............ C12M 23/12
DE   102004020885 A1 * 11/2005  ............ B01L 3/0244
(Continued)

OTHER PUBLICATIONS

Document titled Description DE102004020885A1, machine translation of DE102004020885A1 provided by Espacenet, original document published 2005 (Year: 2005).*
(Continued)

*Primary Examiner* — Holly Kipouros
(74) *Attorney, Agent, or Firm* — Studebaker & Brackett PC

(57) ABSTRACT

A cell transfer device includes a base on which a container accommodating a plurality of cells is mounted, a head with a suction tip attached that sucks the cells in the container, and a control unit that controls the head. The cells are placed on a placement surface that is an upper surface of an underlying culture medium layer including a gel-like culture medium. The control unit acquires information on a height position of the placement surface, specifies a suction height for the cells existing at a first point on the placement surface, and causes the suction tip to suck the cells. Then, the control unit causes the suction tip to suck the cells existing at a second point different from the first point on the placement surface by using the suction height of the first point.

5 Claims, 11 Drawing Sheets

(51) Int. Cl.
*C12M 1/32* (2006.01)
*C12M 3/00* (2006.01)

(56) References Cited

U.S. PATENT DOCUMENTS

| | | |
|---|---|---|
| 2012/0194664 A1 | 8/2012 | Kiyota |
| 2014/0178981 A1 | 6/2014 | Liu et al. |
| 2016/0177254 A1 | 6/2016 | Kiyota |
| 2016/0304821 A1 | 10/2016 | Ito |
| 2017/0159002 A1 | 6/2017 | Ito |
| 2018/0072982 A1* | 3/2018 | Berntsen ............... C12M 47/02 |
| 2018/0126343 A1* | 5/2018 | Wiles .................... B01L 3/5088 |
| 2018/0203028 A1 | 7/2018 | Ito |
| 2020/0048598 A1 | 2/2020 | Sakamoto et al. |

FOREIGN PATENT DOCUMENTS

| | | |
|---|---|---|
| EP | 3 578 955 A1 | 12/2019 |
| JP | 2006-333710 A | 12/2006 |
| JP | 2013-170861 A | 9/2013 |
| WO | 2011/004854 A1 | 1/2011 |
| WO | 2015/087371 A1 | 6/2015 |
| WO | 2017/017990 A1 | 2/2017 |
| WO | 2017/110005 A1 | 6/2017 |
| WO | 2018/163683 A1 | 9/2018 |
| WO | 2018/193718 A1 | 10/2018 |

OTHER PUBLICATIONS

Document titled CN105814188A Subject Moving Device, machine translation of CN105814188A provided by Espacenet, original document published 2016 (Year: 2016).*

Jaklevic et al., Application of Robotics and Automation in a Genomic Laboratory, 1991, Lawrence Berkeley National Laboratory (Year: 1991).*

Molecular Devices, QPix 420 Colony Picking System, 2013 (Year: 2013).*

Wise, Preparing Spread Plates Protocols, 2006, American Society for Microbiology (Year: 2006).*

International Search Report issued in PCT/JP2018/045562; mailed Mar. 12, 2019.

The extended European search report issued by the European Patent Office on Jan. 25, 2021, which corresponds to European Patent Application No. 18902209.8-1132 and is related to U.S. Appl. No. 16/965,188.

* cited by examiner (A)

INPUT LIQUEFIED MATERIAL OF UNDERLYING CULTURE MEDIUM LAYER INTO CONTAINER (B)

STANDBY UNTIL UPPER SURFACE OF UNDERLYING CULTURE MEDIUM LAYER IS FLATTENED (C)

HEAT UNDERLYING CULTURE MEDIUM LAYER WITH HEAT SOURCE FOR GELATION (D) INPUT UPPER CULTURE MEDIUM LAYER CONTAINING CELLS INTO CONTAINER (E) STANDBY UNTIL CELLS LAND ON UPPER SURFACE OF UNDERLYING CULTURE MEDIUM LAYER (F) HEAT UPPER CULTURE MEDIUM LAYER WITH HEAT SOURCE FOR GELATION (G) INPUT LIQUID CULTURE MEDIUM ON UPPER CULTURE MEDIUM LAYER

APPARATUS FOR TREATING BIOLOGICAL MATERIAL

CROSS-REFERENCE TO RELATED APPLICATIONS

This application is a National Stage of International Patent Application No. PCT/JP2018/045562, filed Dec. 11, 2018, which claims priority to Japanese Patent Application No. 2018-012340, filed Jan. 29, 2018, the entire contents of both are incorporated herein by reference.

BACKGROUND

Technical Field

The present disclosure relates to a biological subject treatment device that performs a predetermined treatment on a biological subject such as cells or cell clusters placed in a container.

Background Art

For example, in medical and biological research applications, image capturing processing of cells or cell clusters (example of a biological subject; sometimes simply referred to as "cell") and a treatment of sucking cells and transferring the cells to other locations may be required. For example, the work of capturing images of cells dispersed in a culture medium in a container with an image capturing device, selecting desired cells based on the obtained images, and sucking the selected cells with a tip and transferring the cells to a microplate may be performed as described, for example, in WO 2015/087371 A.

For example, in primary culture of cancer cells (culture immediately after cutting from a specimen), a gel-like culture medium (semi-solid culture medium) containing a growth factor is often used. In this case, the gel-like culture medium containing cells is accommodated in the container, and the cells in the gel-like culture medium are subjected to a treatment such as observation with the image capturing device and suction with the tip.

When a plurality of cells are placed in the gel-like culture medium in the container, the cells are often placed three-dimensionally in the gel-like culture medium. In this case, in a treatment such as cell observation and suction, the height position varies depending on the target cell, and thus there has been a problem that the efficiency of cell treatment decreases.

SUMMARY

Accordingly, the present disclosure improves efficiency of a biological subject treatment in a biological subject treatment device that performs a predetermined treatment on a biological subject placed in a container.

A biological subject treatment device according to one aspect of the present disclosure includes a base on which a container is mounted, the container being configured to accommodate an underlying culture medium layer including a semi-solid or solid culture medium, and a plurality of biological subjects placed at various places on a placement surface that is a flat upper surface of the underlying culture medium layer; a treatment unit configured to perform a predetermined treatment on the plurality of biological subjects placed on the placement surface; and a control unit configured to control an operation of the treatment unit, wherein the control unit acquires position information including a height position of the placement surface; specifies a treatment position on each of the biological subjects existing at a first point on the placement surface based on the position information, and causes the treatment unit to perform the treatment according to the treatment position; and then causes the treatment unit to perform the treatment on each of the biological subjects existing at a second point different from the first point on the placement surface by using the treatment position.

DETAILED DESCRIPTION

Figure 9:
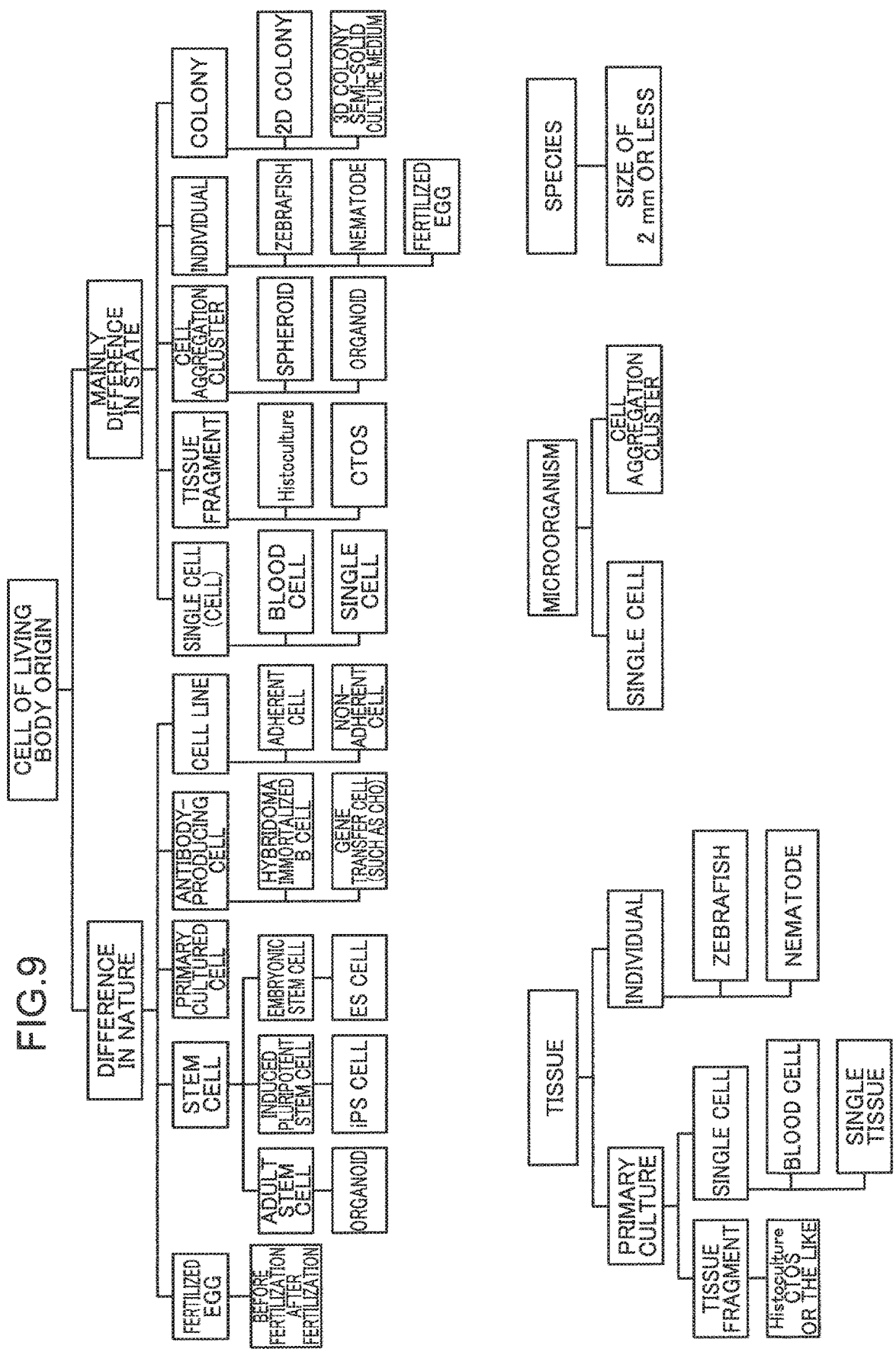
FIG. 9 is a diagram systematically showing examples of biological subjects to which the present disclosure can be applied.

An embodiment of the present disclosure will be described in detail below with reference to the drawings. The biological subject treatment device according to the present disclosure can treat a wide variety of biological subjects. FIG. 9 is a diagram systematically showing examples of biological subjects to which the present disclosure can be applied. As shown in the diagram, in the present disclosure, cells, tissues, microorganisms, small species, and the like of biological origin can be treated. There is no particular limitation on the mode of biological subject treatment. Treatment such as, for example, observation of a biological subject with a camera, suction of a biological subject using a tip, transfer and discharge, administration of a reagent, a growth factor, a growth inhibitory factor, and the like to a biological subject, emission of light beams such as ultraviolet rays can be illustrated. The embodiment described below shows an example in which the biological subject is cells or a cell aggregation cluster formed by aggregating several to several hundred thousand cells (hereinafter, collectively referred to simply as "cell C"), and the mode of the treatment is a transfer treatment of the cell C accompanied by suction of the cell C (cell transfer device).

Overall Structure of Cell Transfer Device

Figure 1:
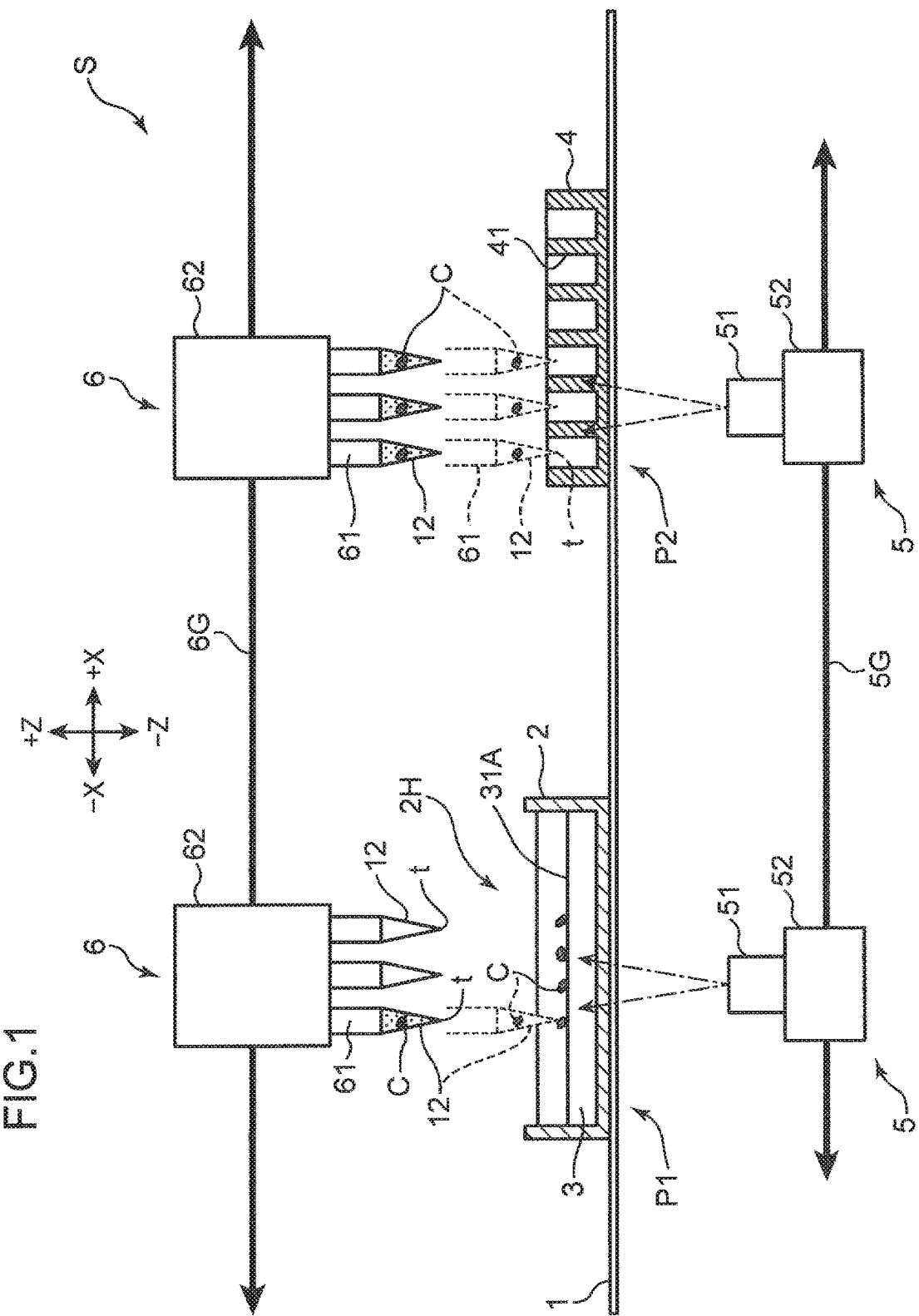
FIG. 1 is a diagram schematically showing a configuration example of a cell transfer device to which the present disclosure is applied.

FIG. 1 is a diagram schematically showing a configuration of a cell transfer device S as one example of a biological subject treatment device according to the present disclosure. Here, the cell transfer device S that transfers a cell C between two containers (container 2 and microplate 4) is illustrated.

The cell transfer device S includes a translucent base 1 having a horizontal mounting surface (upper surface), a camera unit 5 (image capturing unit) disposed below the base 1, and a head unit 6 disposed above the base 1. A transfer source container 2 of the cell C is mounted at a first mounting position P1 of the base 1, and a microplate 4 serving as a transfer destination of the cell C is mounted at a second mounting position P2. The head unit 6 includes a plurality of heads 61 (treatment units) in which suction tips 12 that each suck and discharge the cell C are attached to lower ends, the heads 61 capable of being raised and lowered in an up-and-down direction (Z direction). The camera unit 5 and the head unit 6 are movable in the X direction (horizontal direction) and the direction perpendicular to the plane of FIG. 1 (Y direction). The container 2 and the microplate 4 are mounted on an upper surface of the base 1 within a movable range of the head unit 6.

Roughly, the cell transfer device S is a device in which each of the plurality of suction tips 12 sucks the cell C individually from the container 2 holding the large number of cells C, and transfers the cell C to the microplate 4 (treatment to transfer to a predetermined location), and the plurality of suction tips 12 simultaneously discharge the cells C to the microplate 4 (well 41). Before the suction of the cells C, the cells C held in the container are captured by the camera unit 5, and a sorting operation for sorting good quality cells C to be transferred to the microplate 4 is performed.

Each part of the cell transfer device S will be described below. The base 1 is a rectangular flat plate having predetermined rigidity, and part or all of which is formed of a translucent material. The preferred base 1 is a glass plate. The base 1 is formed of a translucent material such as a glass plate, thereby allowing the camera unit 5 disposed below the base 1 to capture the container 2 and the microplate 4 disposed on an upper surface of the base 1 through the base 1.

The container 2 accommodates a plurality of cells C held in the culture medium 3. The container 2 is, for example, a petri dish, and has an upper surface opening 2H. The culture medium 3 and the cells C are injected into the container 2 and the cells C are sucked by the suction tips 12, through the upper surface opening 2H. The container 2 made of a translucent resin material or glass is used. This is to allow the camera unit 5 to observe the cells C supported in the container 2. The cells C are placed on a flat placement surface 31A in the culture medium 3. The suction tips 12 attached to the head 61 perform a suction treatment (predetermined treatment) on the cells C placed on the placement surface 31A. This will be described in detail later.

The microplate 4 includes a plurality of wells 41 into which the cells C are discharged. The wells 41 are each a bottomed hole opened on an upper surface of the microplate 4. One well 41 accommodates a required number of (usually one) cells C together with the liquid culture medium 3. The microplate 4 made of a translucent resin material or glass is used. This is to allow the camera unit 5 placed below the microplate 4 to observe the cells C supported in the well 41.

The camera unit 5 captures an image of the cells C held in the container 2 or the microplate 4 from the lower surface side thereof, and includes a lens unit 51 and a camera body 52. The lens unit 51 is an object lens used in an optical microscope, and includes a lens group that forms a light image with a predetermined magnification and a lens barrel that accommodates the lens group. The camera body 52 includes an image capturing element such as a CCD image sensor. The lens unit 51 forms a light image of an image capturing target on a light receiving surface of the image capturing element. The camera unit 5 is movable in the X and Y directions below the base 1 along a guide rail 5G extending in the left-right direction parallel to the base 1. In addition, the lens unit 51 is movable in the Z direction for a focusing operation.

The head unit 6 is provided for picking up the cells C from the container 2 and transferring the cells C to the microplate 4, and includes the plurality of heads 61 and a head body 62 to which the heads 61 are assembled. At the tip of each head 61, the suction tip 12 that sucks (pickup) and discharges the cells C is attached. The head body 62 holds the heads 61 so as to be raised and lowered in the +Z and −Z directions, and is movable in the +X and −X directions along a guide rail 6G. Note that the head body 62 is also movable in the Y direction.

Mode of Culture Medium in Container

Figure 2:
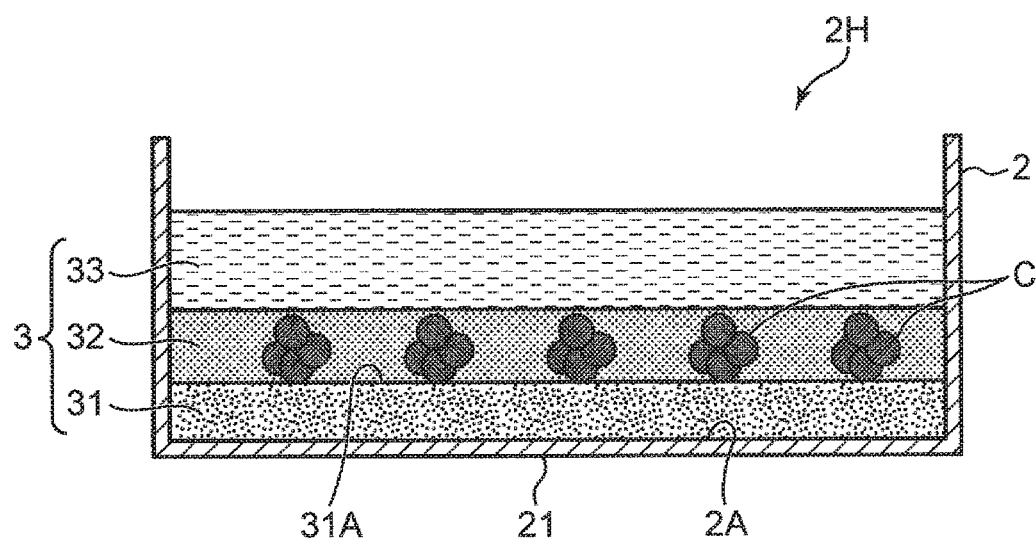
FIG. 2 is a longitudinal cross-sectional view schematically showing a container used in the cell transfer device, and a culture medium and cells accommodated in the container.

FIG. 2 is a longitudinal cross-sectional view schematically showing the culture medium 3 and the plurality of cells C accommodated in the container 2 in the present embodiment. The container 2 includes a flat bottom wall 21 with a uniform thickness. The culture medium 3 illustrates a three-layer structure in FIG. 2, and includes an underlying culture medium layer 31, an upper culture medium layer 32, and a liquid culture medium 33 in order from the lowermost layer.

The underlying culture medium layer 31 includes a solid or semi-solid culture medium, and is in contact with a bottom surface 2A, which is an upper surface of the bottom wall 21. The underlying culture medium layer 31 has a flat upper surface, and the upper surface is the placement surface 31A on which the plurality of cells C are dispersedly placed. The cells C are placed at various places on the placement surface 31A so as to be in contact with the placement surface 31A. The underlying culture medium layer 31 is formed of a translucent material such that the cells C placed on the placement surface 31A can be captured from below by the camera unit 5, in a similar manner to the container 2.

As the underlying culture medium layer 31, a gel-like culture medium (semi-solid culture medium) containing a growth factor and capable of three-dimensionally culturing the cells C can be preferably used. The gel-like culture medium includes, for example, Matrigel (trade name of Corning Incorporated), gel-like culture medium of animal origin such as collagen, gel-like culture medium of plant origin such as hydrogel alginate, and synthetic compounds such as QGel MT 3DMatrix (QGel SA), 3-D Life Biomimetric Hydrogels (trade name of Cellendes GmbH), and Puramatrix (trade name of 3D MATRIX, Ltd). In addition, as the solid culture medium, for example, an agar culture medium, a sponge culture medium, and the like can be used.

The upper culture medium layer 32 is a layer including a semi-solid culture medium stacked on the placement surface 31A of the underlying culture medium layer 31. As the upper culture medium layer 32, the gel-like culture medium described above can also be suitably used. The cells C are placed in the container 2 in a mode of being in contact with the placement surface 31A in the upper culture medium layer 32. That is, the cells C are accommodated in the container 2 in a state where the entire periphery is surrounded by the upper culture medium layer 32 and the underlying culture medium layer 31. That is, a state is formed in which the growth factor is supplied from the entire periphery of the cells C.

The liquid culture medium 33 is a liquid layer injected on the upper culture medium layer 32. As the liquid culture medium 33, various liquid culture media containing a growth factor can be applied.

Figure 3:
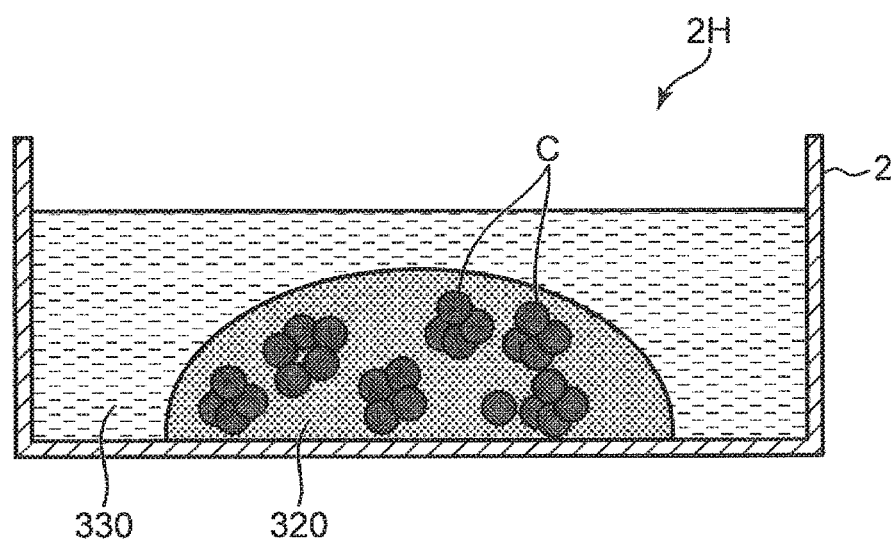
FIG. 3 is a longitudinal cross-sectional view showing a comparative example of a culture medium and cells accommodated in a container.

FIG. 3 is a longitudinal cross-sectional view showing a comparative example of forming a culture medium layer. Here, an example is shown in which the cells C are placed in the container 2 in a mode in which the cells C are three-dimensionally placed in a dome-shaped gel-like culture medium 320, and the periphery of the gel-like culture medium 320 is covered with a liquid culture medium 330. The gel-like culture medium 320 is formed, for example, by dropping the cells C dispersed in the liquid culture medium 320 before gelation onto the bottom surface of the container 2 with a pipette or the like, and then heating and gelling the culture medium. Then, an operation of vertically inverting the container 2 for a predetermined time is performed such that the cells C do not come into contact with the bottom surface of the container 2 (entire periphery of the cells C is surrounded by the culture medium 320). The dome shape is formed by surface tension of the gel-like culture medium 320 and the inversion. Thereafter, the liquid culture medium 330 is injected into the container 2.

The method of the comparative example has an advantage of forming a state in which the cells C are surrounded by the gel-like culture medium while minimizing an amount of expensive gel-like culture medium used. However, the cells C overlap with each other in the up-and-down direction in the gel-like culture medium 320, which makes it difficult to individually observe the cells C by image capturing with the camera unit 5. Also, it is difficult to suck the cells C with the suction tip 12. In contrast, in the mode of forming the culture medium layers of the present embodiment shown in FIG. 2, the cells C are two-dimensionally placed on the placement surface 31A of the underlying culture medium layer 31. The upper culture medium layer 32, which is a material of the same quality as the underlying culture medium layer 31, has a high affinity, and it is not necessary to invert the container 2 as described above. Therefore, the upper culture medium layer 32 is not transformed into a dome shape, and the two-dimensional placement of the cells C is maintained. Therefore, the present embodiment has an advantage that it is easy to perform the image capturing operation by the camera unit 5 and the suction operation by the suction tip 12 on each cell C.

Example of Forming Culture Medium

Figure 4A:
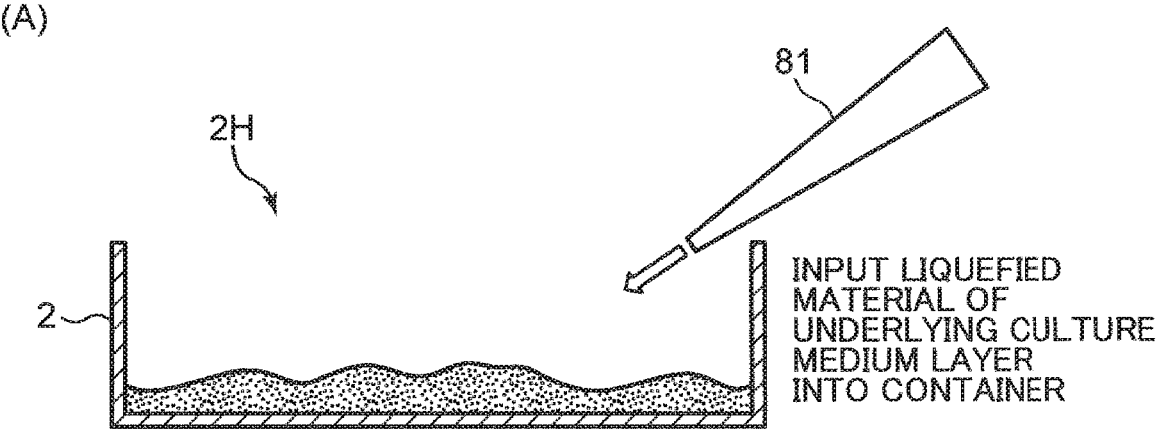
FIG. 4A is a diagram showing procedures (A) to (C) for forming layers of the culture medium in the container.
Figure 4A:
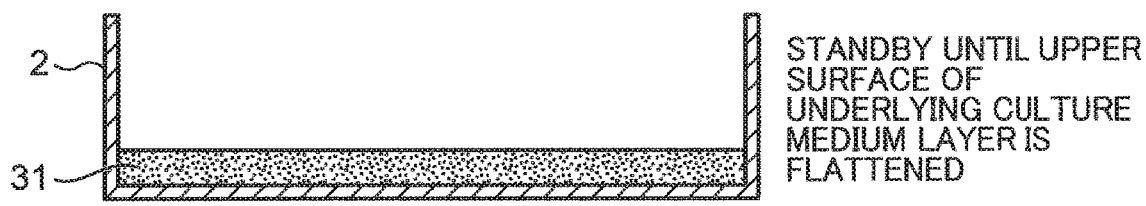
Figure 4A:
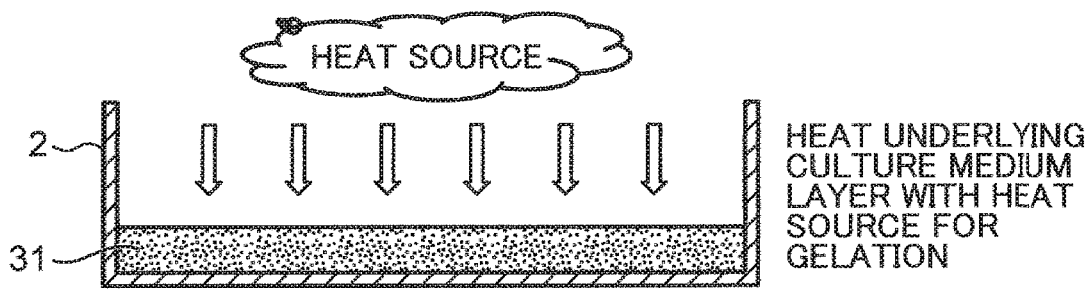
Figure 4B:
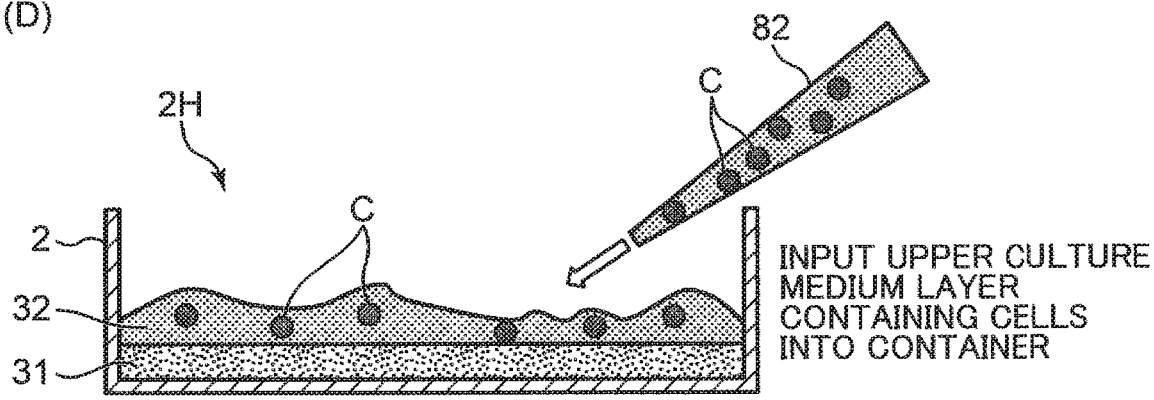
FIG. 4B is a diagram showing procedures (D) to (G) for forming layers of the culture medium in the container.
Figure 4B:
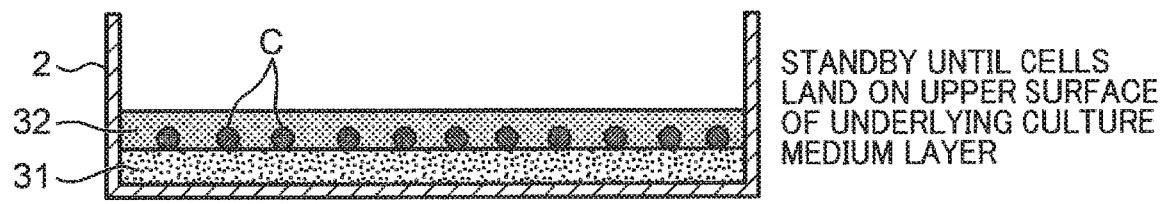
Figure 4B:
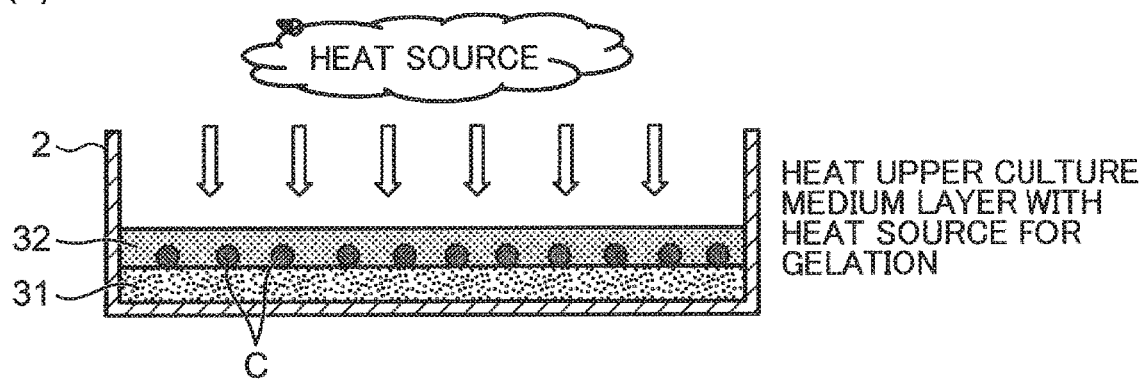
Figure 4B:
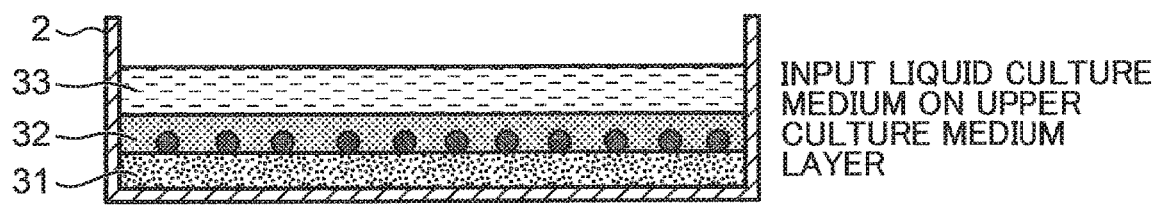

Subsequently, an example of forming the culture medium 3 having a three-layer structure illustrated in FIG. 2 will be described. FIGS. 4A and 4B are diagrams showing procedures (A) to (G) of forming layers of the culture medium 3 in the container 2. Here, an example is shown in which the underlying culture medium layer 31 and the upper culture medium layer 32 are formed by a gel-like culture medium. The gel-like culture medium has a property of being a liquid at low temperatures equal to or lower than a predetermined temperature and gelling when heated to equal to or higher than the predetermined temperature. Matrigel described above has a property of being a liquid at temperatures equal to or lower than 8° C., starting gelation at 8° C. to 10° C., and quickly gelling at 22° C. to 35° C.

First, as shown in the procedure (A), the container 2 is mounted on a horizontal table (base 1), and a predetermined amount of liquefied gel-like culture medium constituting the underlying culture medium layer 31 is injected into the container 2 through the upper surface opening 2H by using a pipette tip 81. When Matrigel is used as the gel-like culture medium, the gel-like culture medium is injected while being cooled to 8° C. or less. For example, when the container 2 is a petri dish with a diameter of 35 mm, the gel-like culture medium solution of 400 µl (microliter) is injected, and the underlying culture medium layer 31 with a thickness of about 0.3 mm to 0.5 mm is formed in the container 2. Then, as shown in the procedure (B), a standby state is kept until the upper surface of the liquid underlying culture medium layer 31 (surface serving as the placement surface 31A) is flattened.

Subsequently, as shown in the procedure (C), a treatment of heating the liquid underlying culture medium layer 31 for a predetermined time by using a heat source to cause the underlying culture medium layer 31 to gel is performed. When the gel-like culture medium is Matrigel with the liquid amount as described above, the gel-like culture medium can gel by performing a heat treatment at 37° C. for about 15 minutes.

Next, as shown in the procedure (D), the liquid to constitute the upper culture medium layer 32 is injected into the container 2 by using a pipette tip 82. At this time, a cell suspension in which the cells C are dispersed in the upper culture medium layer 32 is discharged from the pipette tip 82 to the container 2. For example, a cell suspension in which the cells C are dispersed in liquid Matrigel is prepared, which is sucked by the pipette tip 82 and discharged into the container 2. By this injection, the liquid layer containing the cells C, which subsequently becomes the upper culture medium layer 32, is formed on the underlying culture medium layer 31 that has undergone gelation. Note that if the container 2 is a petri dish with a diameter of 35 mm, the gel-like culture medium solution of 400 µl in which the cells C are dispersed is injected, and the upper culture medium layer 32 with a thickness of about 0.3 mm to 0.5 mm is formed in the container 2.

Thereafter, as shown in the procedure (E), a standby state is kept until the cells C contained in the liquid upper culture medium layer 32 settle down by the gravity and land on the upper surface of the underlying culture medium layer 31 (placement surface 31A). The cells C are two-dimensionally placed on the upper surface by the landing on the upper surface. When the cells C have completed the landing, as shown in the procedure (F), a heat treatment of heating the liquid upper culture medium layer 32 with a heat source for a predetermined time is performed. When the gel-like culture medium is Matrigel with the liquid amount as described above, the heat treatment is a heat treatment at 37° C. for about 15 minutes. This allows the liquid upper culture medium layer 32 containing the cells C to gel.

Then, as shown in the procedure (G), the liquid culture medium 33 is injected into the container 2. For the petri dish, an amount of the injection is about 3 ml. By the above procedures (A) to (G), the culture medium 3 having a three-layer structure is formed on the bottom wall 21 of the container 2.

Figure 5A:
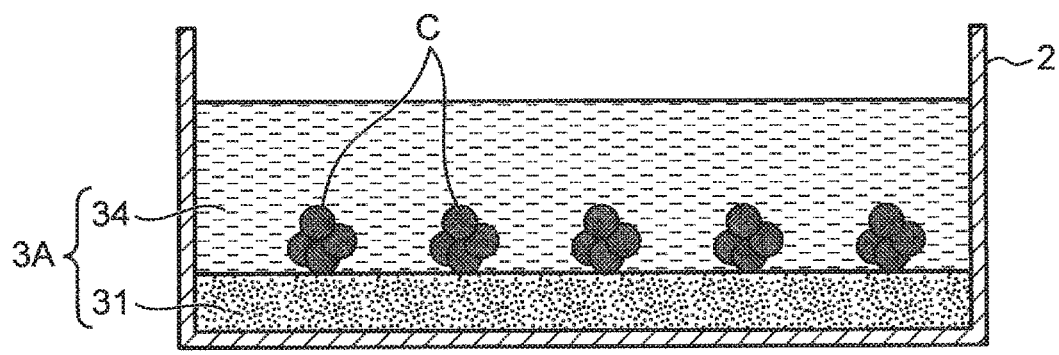
FIGS. 5A and 5B are longitudinal cross-sectional views showing another example of forming culture medium layers in the container.
Figure 5B:
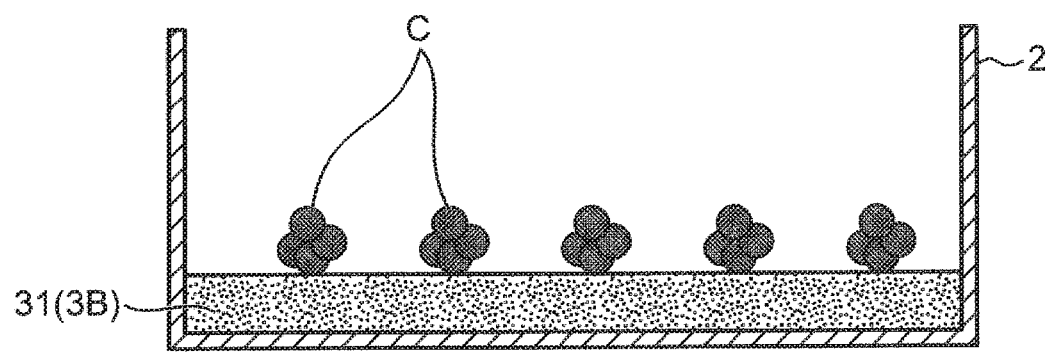

FIGS. 5A and 5B are longitudinal cross-sectional views showing other examples of forming the culture medium layer in the container 2. These modifications show examples in which the gel-like culture medium is only one layer of the underlying culture medium layer 31. The culture medium 3A illustrated in FIG. 5A includes the underlying culture medium layer 31 and the upper liquid culture medium layer 34 formed by injecting a liquid onto the underlying culture medium layer 31. The cells C are placed in the container 2 in a mode of settling down on the upper surface of the underlying culture medium layer 31 (placement surface 31A) in the upper liquid culture medium layer 34. The upper liquid culture medium layer 34 can be formed, for example, by diluting the cell suspension in which the cells C are dispersed in the liquid culture medium or the cell suspension in which the cells C are dispersed in liquid Matrigel with a liquid culture medium.

The culture medium 3B illustrated in FIG. 5B includes only the underlying culture medium layer 31. The cells C are placed in a mode of being grounded on the upper surface of the underlying culture medium layer 31 (placement surface 31A). In this modification, for example, a sponge culture medium is used as the underlying culture medium layer 31. The culture medium 3B can be formed by laying the sponge culture medium on the bottom wall 21 of the container 2 and then sprinkling the cell suspension containing the cells C from above the sponge culture medium. In this case, the sponge culture medium absorbs the growth factor in the container and supplies the growth factor to the cells C.

Configuration of Image Capturing System

Figure 6:
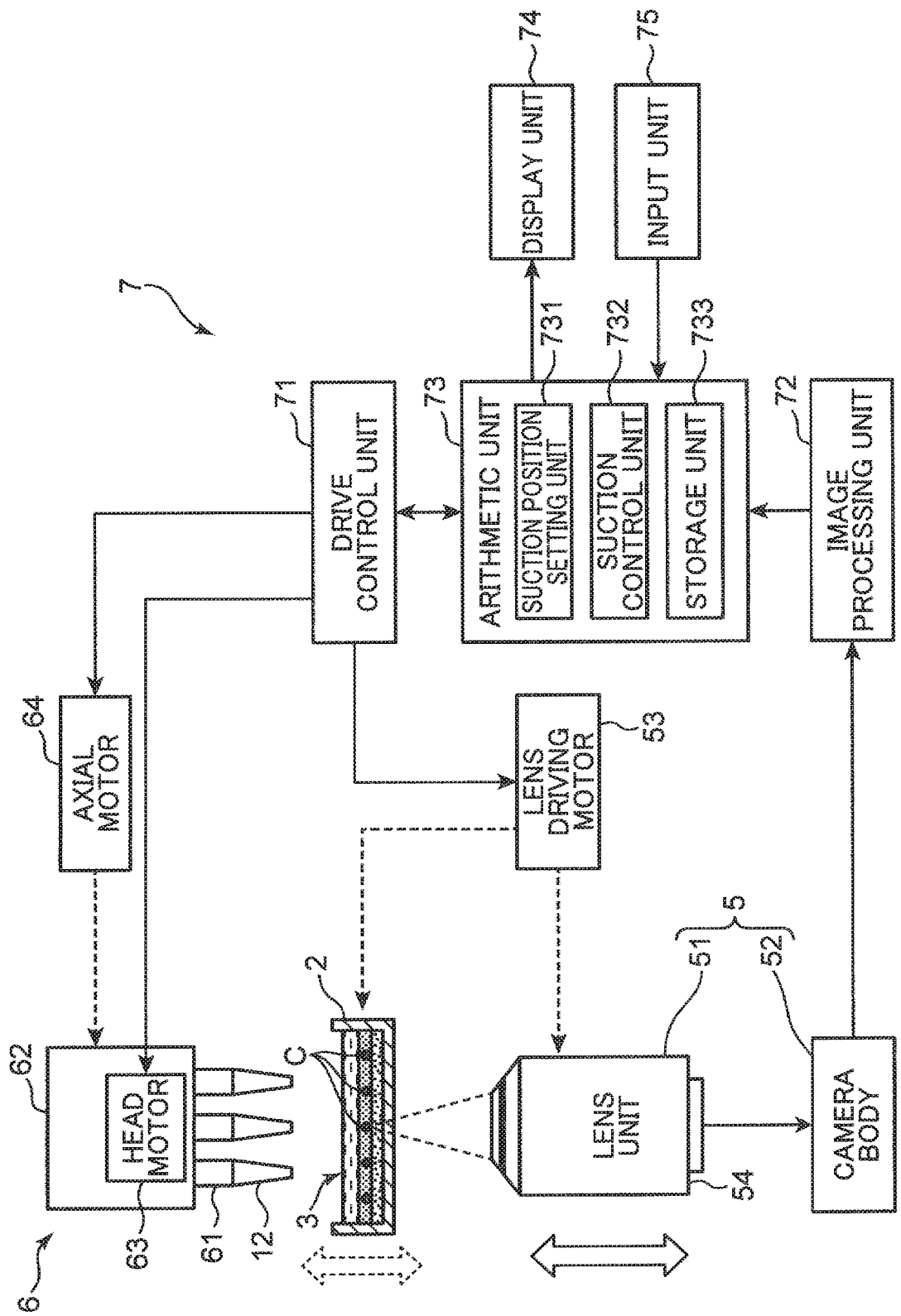
FIG. 6 is a block diagram of an image capturing system applied to the cell transfer device.

FIG. 6 is a block diagram of an image capturing system applied to the cell transfer device S. The image capturing system includes the camera unit 5 that captures the image capturing target on an image capturing optical axis, a control unit 7 that controls an operation of the lens unit 51 and performs predetermined processing based on image information acquired by the camera body 52, a lens driving motor 53 that moves the lens unit 51 up and down, a display unit 74, and an input unit 75.

FIG. 6 shows the container 2 that accommodates the culture medium 3 having a three-layer structure shown in FIG. 2 and the cells C as the image capturing target. That is, the camera unit 5 captures the cells C supported by the culture medium 3 in the thickness direction of the culture medium 3 (underlying culture medium layer 31). Note that the control unit 7 also controls the suction operation of the cells C by the head 61 (treatment unit) to which the suction tip 12 is attached and the moving operation in the horizontal direction (one example of predetermined treatment) by controlling a head motor 63 in the head unit 6 and an axial motor 64.

The lens driving motor 53 rotates forward or backward to move the lens unit 51 in an up-and-down direction with a predetermined resolution via a power transmission mechanism (not shown). By this movement, the focus position of the lens unit 51 is adjusted to the cells C supported in the container 2. Note that as shown by the dotted line in FIG. 6, the container 2 itself or the stage on which the container 2 is mounted (base 1) may be moved up and down, not by the lens unit 51 but by another motor that substitutes the lens driving motor 53.

The head motor 63 is a motor that serves as a drive source for the raising and lowering operation of the heads 61 with respect to the head body 62, and for the operation of generating suction force and discharge force at a tip opening t of the tips 12 attached to the head 61. The axial motor 64 is a motor that serves as a drive source for moving the head unit 6 (head body 62) along the guide rail 6G (FIG. 1).

The control unit 7 includes, for example, a personal computer or the like, and operates to functionally include a drive control unit 71, an image processing unit 72, and an arithmetic unit 73 by executing a predetermined program.

The drive control unit 71 controls operations of the lens driving motor 53, the head motor 63, and the axial motor 64. Specifically, the drive control unit 71 gives control pulses for moving the lens unit 51 in an up-and-down direction at a predetermined pitch (for example, tens of μm pitch) to the lens driving motor 53 for the focusing operation. Also, although not shown in FIG. 6, the drive control unit 71 also controls the operation of a camera axis drive motor that moves the camera unit 5 along the guide rail 5G. Furthermore, the drive control unit 71 also controls mechanical operations of the head unit 6. The drive control unit 71 controls the head motor 63 to control the raising and lowering operation of the heads 61 and the operation of generating suction force or discharge force at the tip opening t of the tips 12.

The image processing unit 72 performs image processing such as edge detection processing and pattern recognition processing with feature amount extraction on image data acquired by the camera body 52. The image processing unit 72 acquires the image data of the container 2 in which the cells C are placed on the placement surface 31A of the underlying culture medium layer 31, and recognizes the cells C existing on the placement surface 31A by the image processing. This makes it possible to determine XY coordinates of each cell C placed on the placement surface 31A. This also makes it possible to evaluate the quality of the cells C and the like.

The arithmetic unit 73 mainly performs processing of acquiring position information including the position of the cells C in the container 2 in the horizontal direction (XY coordinates), and the position of the cells C in the height direction, that is, in the present embodiment, the height position of the placement surface 31A of the underlying culture medium layer 31 (Z coordinates), and specifying the suction position of the cells C by the suction tip 12 (treatment position on a biological subject), and performs processing of controlling the suction operation. The arithmetic unit 73 functionally includes a suction position setting unit 731, a suction control unit 732, and a storage unit 733.

The suction position setting unit 731 specifies the suction position of the cells C by the suction tip 12 from information on XY coordinates of the cells C on the placement surface 31A and information on Z coordinates of the placement surface 31A, which have been obtained from the image processing unit 72. As will be described later, the Z coordinate information on the placement surface 31A is acquired from information input from the input unit 75 to the arithmetic unit 73 (input information), or focusing position information (actually measured information) obtained by capturing the image of the placement surface 31A by using the camera unit 5.

The suction control unit 732 performs processing of acquiring the XYZ coordinates indicating the suction position specified by the suction position setting unit 731 and setting a suction sequence of the cells C. In the present embodiment, the suction control unit 732 detects the cell C that can share the Z coordinate from among the plurality of cells C that are dispersedly placed on the placement surface 31A, thereby setting the efficient suction sequence.

Specifically, the suction control unit 732 specifies the suction position of the cell C existing at a specified first point on the placement surface 31A based on the XYZ coordinates, and causes the head 61 (suction tip 12) to perform a first suction operation according to the suction position. Then, the suction control unit 732 sets the suction sequence that causes the suction tip 12 to perform a second suction operation on the cell C existing at a second point different from the first point on the placement surface 31A by using the Z coordinate used in the suction operation at the first point.

The suction sequence is given to the drive control unit 71. Based on the suction sequence, the drive control unit 71 controls the head unit 6 (head 61) to perform the suction operation on the cell C. Specifically, the drive control unit 71 lowers the head 61 according to the suction position (Z coordinate) set for the cell C at the first point, causes the suction tip 12 to suck the cell C, and then raises the head 61 (first suction operation). Subsequently, the drive control unit 71 moves the head 61 in the horizontal direction based on the XY coordinates set for the cell C at the second point, further lowers the head 61 according to the Z coordinate used, and causes the suction tip 12 to suck the cell C (second suction operation).

The storage unit 733 stores the input information given by the operator to the input unit 75, the focusing position information acquired from the camera unit 5, various pieces of setting information, and other information. Also, the storage unit 733 stores information regarding the size of the container 2 used in the cell transfer device S (inner diameter, height, and the like of the container) in association with a model number and the like. Furthermore, the storage unit 733 stores the XYZ coordinates indicating the suction position set by the suction position setting unit 731.

The display unit 74 is a display that displays images captured by the camera unit 5. In the present embodiment, an image of the container 2 supporting the cell C captured by the camera unit 5, and other images are displayed.

The input unit 75 includes a keyboard, a mouse, or the like, and receives input of various pieces of information including information on the setting of the suction position from the operator. Specifically, the input unit 75 receives input of model number information on the container 2, thickness information on the bottom wall 21 (height position of the bottom surface 2A), information about the height position of the placement surface 31A of the underlying culture medium layer 31, and other information. Also, the input unit 75 receives input regarding a selection operation of which cell C among the cells C displayed on the display unit 74 is to be transferred.

[Method of Setting Suction Height Position]

Figure 7A:
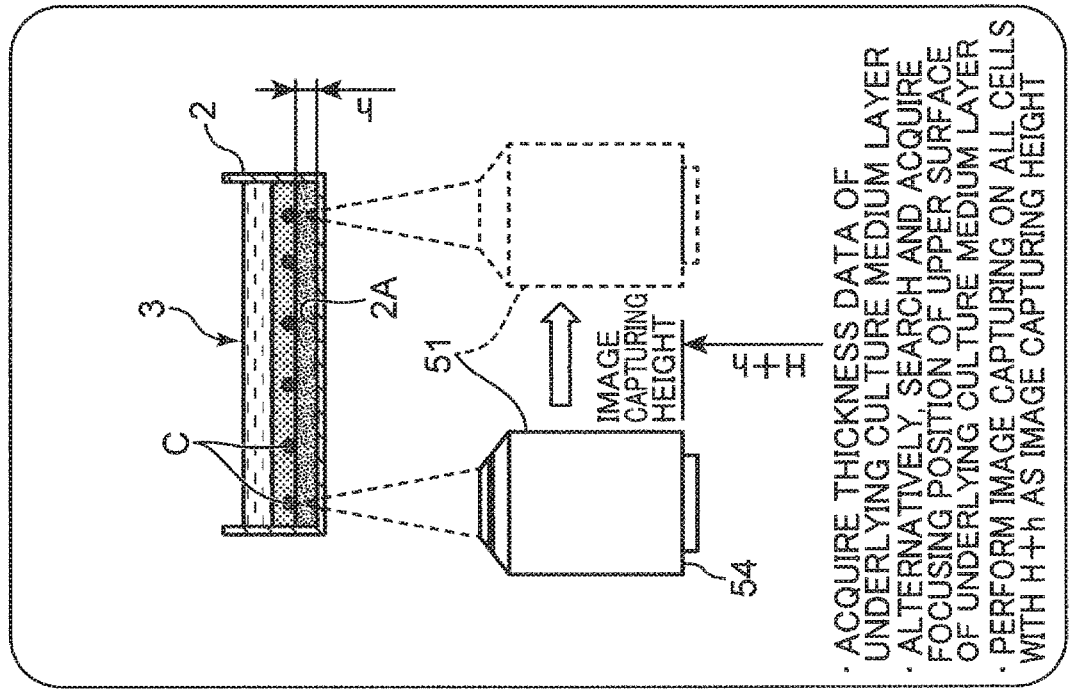
FIG. 7A is a diagram schematically showing cell suction procedures (1) and (2) by the cell transfer device.
Figure 7B:
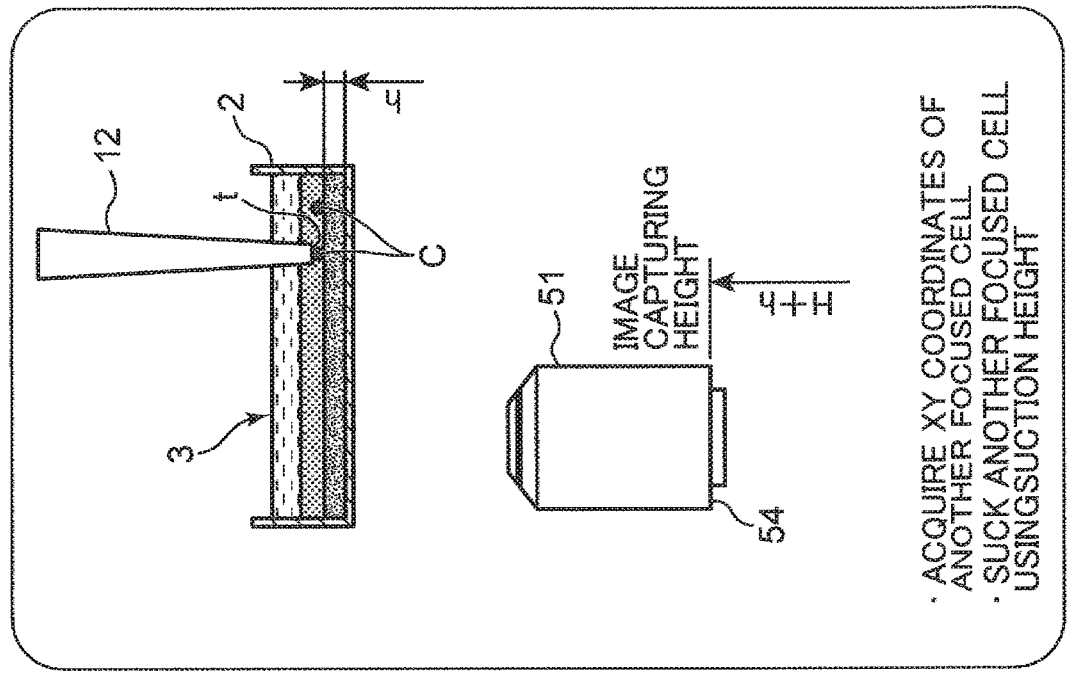
FIG. 7B is a diagram schematically showing cell suction procedures (3) and (4) by the cell transfer device.
Figure 7B:
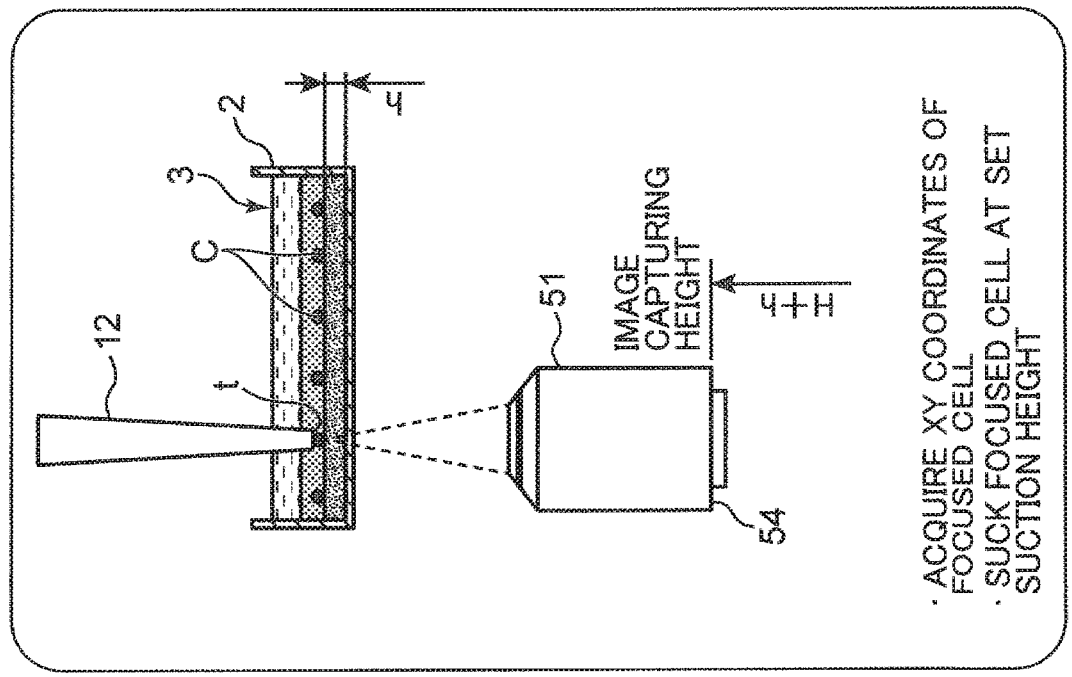

FIGS. 7A and 7B are diagrams schematically showing the suction procedures (1) to (4) of the cells C by the cell transfer device S, including the method of setting the suction height position of the cells C by the suction tip 12. In the present embodiment, since the cells C are sucked from the placement surface 31A, which is the upper surface of the underlying culture medium layer 31, in order to set the suction height, the height position (Z coordinate) of the placement surface 31A needs to be determined. Since the height position of the placement surface 31A is the height position of the upper surface of the underlying culture medium layer 31 accommodated in the container 2, in order to specify the height position, the height position of the bottom surface 2A of the container 2 (thickness of the bottom wall 21) and the thickness information on the underlying culture medium layer 31 are required. Such information can be acquired by:

(method A) a method of depending on input information from the input unit 75;

(method B) a method of calculation by the arithmetic unit 73 doing arithmetic on the input information;

(method C) a method of determination by actual measurement using the camera unit 5; or other methods.

The procedure (1) of FIG. 7A shows the method C of acquiring the height position of the bottom surface 2A of the container 2. In this case, the camera unit 5 performs image capturing on the bottom surface 2A of the container 2. Then, the suction position setting unit 731 acquires the height position of the bottom surface 2A based on focus position information of the lens unit 51 with respect to the bottom surface 2A. The focal position of the lens unit 51 is defined by the parfocal distance from a mounting surface 54 to the image capturing target (here, the bottom surface 2A). If the lens unit 51 is focused on the bottom surface 2A, the distance between the bottom surface 2A and the mounting surface 54 becomes the parfocal distance. Therefore, the height position of the bottom surface 2A can be measured with the height position of the mounting surface 54 defined as the reference height H.

Specifically, the suction position setting unit 731 controls the lens driving motor 53 through the drive control unit 71 to cause the camera body 52 to perform the image capturing operation on the container 2 while moving the lens unit 51 in the up-and-down direction at a predetermined pitch. The image processing unit 72 determines the contrast between pixels for each image data acquired for each movement pitch of the lens unit 51, and specifies the image of the bottom surface 2A with the highest contrast as the focused image. The suction position setting unit 731 sets the height position of the mounting surface 54 when the focused image is acquired as the reference height H. Then, the suction position setting unit 731 sets the focusing position of the lens unit 51 at the lowering position of the tip opening t of the suction tip 12 attached to the head 61, that is, the suction position. With this operation, the height position at which the lens unit 51 is focused is associated with the suction position such that the height position becomes the suction position. Setting values of the reference height H and the suction position are stored in the storage unit 733.

When the procedure (1) is executed by the method A, the input unit 75 receives input of container bottom information regarding the height position of the bottom surface 2A. For example, thickness information on the bottom wall 21 of the container 2 (container bottom information) is directly input by the operator, or the thickness information on the container 2 is read from the storage unit 733 based on input of the model number of the container 2 or the like, whereby the container bottom information is acquired. For example, if the parfocal distance of the lens unit 51 with respect to the upper surface of the base 1 is known, the height position of the bottom surface 2A can be determined by considering the thickness of the bottom wall 21.

The procedure (2) shows a method of acquiring the height position (position information) of the placement surface 31A of the underlying culture medium layer 31. The height position of the placement surface 31A can be simply specified based on the input information on a thickness h of the underlying culture medium layer 31 given from the input unit 75 (method A). That is, since the reference height H is determined by the procedure (1), if the information on the thickness h is given, the height position of the placement surface 31A can be acquired from H+h.

Even if the thickness h is not directly input from the input unit 75, the height position of the placement surface 31A can be acquired from related information (method B). For example, when the input unit 75 receives input of information about the shape of the container 2 (such as size of inner diameter of the container) and information about the input amount of the material corresponding to the underlying culture medium layer 31 to the container 2, the height position of the placement surface 31A from the bottom surface 2A is naturally determined. Therefore, the suction position setting unit 731 can calculate the height position of the placement surface 31A based on these pieces of input information.

Furthermore, the height position of the placement surface 31A can be acquired by actual measurement using the camera unit 5 (method C). In this case, the suction position setting unit 731 acquires the height position of the placement surface 31A based on the focus position information about the placement surface 31A. Specifically, the suction position setting unit 731 causes the camera body 52 to perform the image capturing operation on the container 2 while moving the lens unit 51 in an up-and-down direction at a predetermined pitch, and specifies an image of the placement surface 31A or the cells C placed on the placement surface 31A with the highest contrast as the focused image. Then, the height position when the focused image is acquired can be set as the height position of H+h that is obtained by adding the thickness h of the underlying culture medium layer 31 to the reference height H.

Note that if another translucent member other than air is interposed on the image capturing optical axis of the lens unit 51, since an optical path is refracted in accordance with a refractive index of the translucent member, the focal position of the lens unit 51 extends far away. When the method C is adopted in the procedures (1) and (2), since the bottom wall 21 of the container 2 and the underlying culture medium layer 31 are interposed on the image capturing optical axis, a focal point extension amount due to the interposition is preferably added to the parfocal distance. That is, the height position obtained by correcting the height position of the mounting surface 54 with the focal point extension amount is preferably used as the reference height H.

If the height of H+h is determined by any of the methods A to C, the suction position setting unit 731 causes the camera unit 5 to perform image capturing on all the cells C supported in the container 2 with H+h as the image capturing height that is the height position of the mounting surface 54. An angle of view of the lens unit 51 used for this type of image capturing is generally narrow, and it is not possible to capture the entire area of the container 2 with one image capturing. Therefore, the image capturing is executed so as to cover the entire area of the container 2 in a plurality of times.

The procedure (3) shown in FIG. 7B shows the suction operation of the cell C. The suction position setting unit 731 specifies the focused cell C in the image obtained by image capturing at the image capturing height H+h by referring to, for example, the contrast between each cell C and surroundings thereof. Then, the suction position setting unit 731 acquires the XY coordinate of the focused cell C based on an image processing result by the image processing unit 72. Note that the Z coordinates of the focused cell C are all coordinates corresponding to H+h.

The XYZ coordinates of the focused cells C obtained as described above are given to the suction control unit 732. The suction control unit 732 sets the suction sequence for sequentially sucking the focused cells C, that is, the cells C for which the Z coordinates can be used. Then, based on the suction sequence, the suction control unit 732 moves the head 61 in the XY direction so as to agree with the XY coordinates of the cells C at the first point of the placement surface 31A, and thereafter lowers the head 61. In the procedure (1), since the focusing position (H+h) is associated with the suction height by the tip opening t of the suction tip 12 such that the focusing position (H+h) becomes the suction height by the tip opening t of the suction tip 12, the head 61 is lowered to the Z coordinate position corresponding to H+h. After the head 61 is lowered, the suction control unit 732 generates suction force at the tip opening t, sucks the cells C at the first point into the suction tip 12, and then raises the head 61.

The procedure (4) shows that the suction operation of the cell C at the second point different from the first point is executed by using the suction height of the cell C at the first point. The suction control unit 732 moves the head 61 in the XY direction so as to agree with the XY coordinates of the cell C at the second point, and then lowers the head 61. As the suction height, the suction height when sucking the cell C at the first point is used. Then, the suction control unit 732 generates suction force at the tip opening t, sucks the cell C at the second point into the suction tip 12, and then raises the head 61. The suction operation on the remaining focused cells C is similarly performed.

All the cells C supported in the container 2 do not always exist at the position where the cells are focused at the image capturing height H+h. Cells C that are at a position floating from the placement surface 31A, or cells C that are at a position that falls lower than the placement surface 31A can exist. The suction position setting unit 731 causes the camera unit 5 to capture again cells C that are not focused at the image capturing height H+h, and reacquires the Z coordinate of each cell C. The suction control unit 732 corrects the suction height based on the reacquired Z coordinate, and performs the suction operation on each cell C.

[Flow Chart of Suction Operation]

Figure 8:
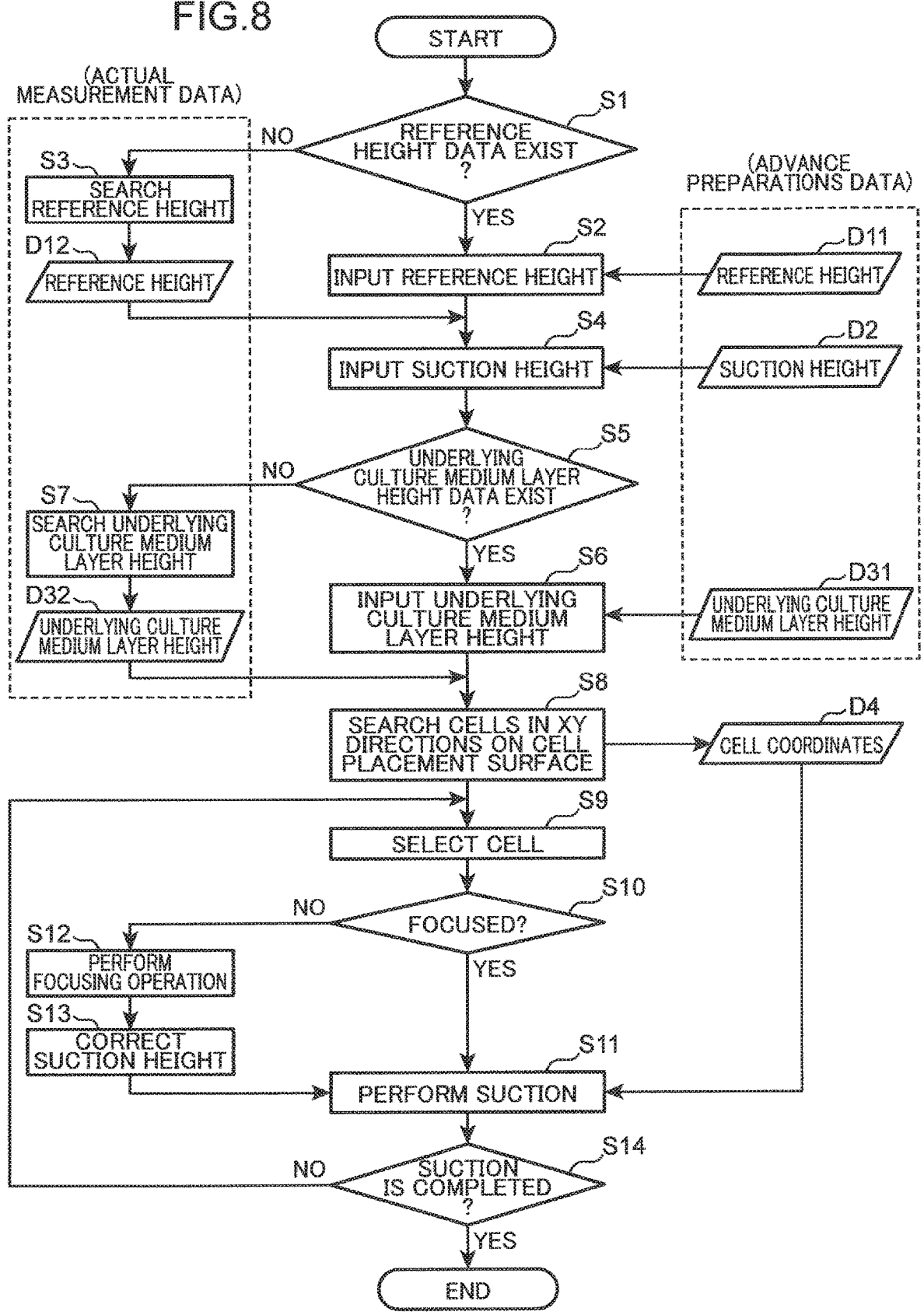
FIG. 8 is a flowchart showing an operation of the cell transfer device.

FIG. 8 is a flowchart showing the suction operation of the cells C by the cell transfer device S. When the process starts, the suction position setting unit 731 of the arithmetic unit 73 determines whether data on the reference height H shown in the procedure (1) of FIG. 7A exists (step S1). When the height position (thickness) of the bottom surface 2A of the container 2 is known, and based on this, the data on the reference height H is obtained as advance preparations data (YES in step S1), the suction position setting unit 731 receives input of data D11 on the reference height H from the input unit 75 (step S2).

On the other hand, when the data on the reference height H does not exist (NO in step S1), the suction position setting unit 731 controls the camera unit 5 to perform the process of searching the reference height H (step S3) by the method described in the case of adopting the method C in the procedure (1). With this operation, data D12 on the reference height H will be acquired by actual measurement.

Subsequently, the suction position setting unit 731 receives input of suction height data D2 for sucking the cells C at the tip opening t of the suction tip 12 (step S4). As described above, the suction height data D2 is data for setting the focusing position of the lens unit 51 at the suction position of the suction tip 12.

Next, the suction position setting unit 731 determines whether data on the thickness h of the underlying culture medium layer 31 exists (step S5). When the thickness h is obtained as advance preparations data from the model number of the container 2 or the input amount of the culture medium material (YES in step S5), the suction position setting unit 731 receives input of data D31 on the thickness h of the underlying culture medium layer 31 from the input unit 75 (step S6).

On the other hand, when the data on the thickness h does not exist (NO in step S5), the suction position setting unit 731 controls the camera unit 5 to perform the process for searching the thickness h by the method described in the case of adopting the method C in the procedure (2) (step S7). With this operation, data D32 on the thickness h of the underlying culture medium layer 31 is acquired by actual measurement. The image capturing height H+h is obtained by combination of the data D11 or data D12 and the data D31 or data D32.

Thereafter, the suction position setting unit 731 sets the lens unit 51 at the image capturing height H+h and causes the camera unit 5 to capture an image of the container 2. The image processing unit 72 performs image processing on the image obtained by the image capturing, thereby specifying the cells C existing on the placement surface 31A of the underlying culture medium layer 31. Then, the suction position setting unit 731 acquires the XY coordinates of the cells C (search the cells C) based on an image processing result by the image processing unit 72 (step S8). With this operation, data D4 on XYZ coordinates indicating the position of each cell C is acquired.

Then, the suction control unit 732 sets the suction sequence that determines the suction order of the cells C on the placement surface 31A, and according to the suction sequence, the suction control unit 732 selects the cell C (cell at the first point) to be sucked by the suction tip 12 (step S9). Subsequently, the suction control unit 732 determines whether the selected cell C is captured in a focused state, that is, whether the suction height may be set at a height corresponding to the image capturing height H+h (step S10). When the cell C is in a focused state (YES in step S10), the suction control unit 732 causes the suction tip 12 to perform the operation of sucking the cell C (step S11).

On the other hand, when the cell C is not in a focused state (NO in step S10), the suction position setting unit 731 causes the camera unit 5 to perform the image capturing and focusing operation on the cell C again, and newly acquires the Z coordinate of the cell C (step S12). Then, the suction position setting unit 731 corrects the suction height based on the reacquired Z coordinate (step S13), and performs the suction operation on the cell C (step S11).

Thereafter, it is confirmed whether the suction of the transfer target cell C existing on the placement surface 31A is completed (step S14). When the suction is not completed (NO in step S14), returning to step S9, next cells C (cells at the second point) existing at an XY position different from the previous cells C on the placement surface 31A are selected, and the suction operation is performed. When these cells C are focused cells C, the Z coordinate used for the previous cells C is used. On the other hand, when the suction is completed (YES in step S14), the process ends.

Operational Effects

With the cell transfer device S (biological subject treatment device) according to the present embodiment described above, the cells C are placed on the placement surface 31A, which is the flat upper surface of the underlying culture medium layer 31, in the container 2. The suction position setting unit 731 of the control unit 7 acquires information on the height position (H+h) of the placement surface 31A, and causes the cells C at the first point to be sucked based on the height position. Then, by using the height position (H+h) used for sucking the cells C at the first point, the suction position setting unit 731 causes the head 61 to perform the suction operation of the cells C existing at the second point different from the first point. Therefore, it is possible to simplify the specifying of the suction height for the plurality of cells C, and to improve the suction work efficiency of the cells C.

Disclosure Included in the Above Embodiment

Note that the above-described specific embodiment mainly includes the disclosure having the following configurations.

A biological subject treatment device according to one aspect of the present disclosure includes a base on which a container is mounted, the container being configured to accommodate an underlying culture medium layer including a semi-solid or solid culture medium, and a plurality of biological subjects placed at various places on a placement surface that is a flat upper surface of the underlying culture medium layer; a treatment unit configured to perform a predetermined treatment on the plurality of biological subjects placed on the placement surface; and a control unit configured to control an operation of the treatment unit, wherein the control unit acquires position information including a height position of the placement surface; specifies a treatment position on each of the biological subjects existing at a first point on the placement surface based on the position information, and causes the treatment unit to perform the treatment according to the treatment position; and then causes the treatment unit to perform the treatment on each of the biological subjects existing at a second point different from the first point on the placement surface by using the treatment position.

With this biological subject treatment device, the biological subject is placed on the placement surface, which is the flat upper surface of the underlying culture medium layer, in the container. The control unit acquires the position information including the height position of the placement surface, and specifies the treatment position on the biological subject at the first point based on the position information. Then, the control unit causes the treatment unit to perform the treatment on the biological subject existing at the second point by using the treatment position obtained at the first point. Therefore, it is possible to simplify the specifying of treatment positions for the plurality of biological subjects and to improve the efficiency of treatment of the biological subjects.

The biological subject treatment device may further include an input unit configured to input information to the control unit, in which the control unit acquires the position information based on input information about a thickness of the underlying culture medium layer given from the input unit.

With the biological subject treatment device, the control unit can easily acquire the position information including the height position of the placement surface. Also, by storing the position information, even in the treatment on a biological subject using another container having the same shape, the treatment position can be specified by using the position information.

In this case, the control unit preferably acquires the position information by receiving, from the input unit, input of information about a shape of the container and information about an input amount of a material corresponding to the underlying culture medium layer to the container, and calculating the height position of the placement surface based on the information.

With the biological subject treatment device, the height position of the placement surface is determined by calculation from the information on the container shape given from the input unit and the input of the material of the underlying culture medium layer. Therefore, the control unit can easily acquire the position information even in a treatment environment in which the type of the container and the input amount are different.

In the biological subject treatment device, the control unit preferably receives input of container bottom information including a height position of a bottom surface of the container, and specifies the height position of the placement surface on the base from the input information about the thickness of the underlying culture medium layer and the container bottom information.

Since the underlying culture medium layer is accommodated in the container and the container is mounted on the base, when specifying the height position of the placement surface on the base, it may be necessary to consider the height position of the bottom surface of the container. With the biological subject treatment device, the control unit can easily acquire the container bottom information.

In the biological subject treatment device, the container and the underlying culture medium layer may be formed of a translucent material, the biological subject treatment device may further include an image capturing unit configured to capture an image of the underlying culture medium layer accommodated in the container in a thickness direction of the underlying culture medium layer, and the control unit may acquire the position information based on focus position information of the image capturing unit with respect to the placement surface.

With the biological subject treatment device, the position information can be acquired by using the image capturing unit included in the biological subject treatment device. Therefore, the control unit can easily acquire the position information even in a treatment environment in which the type of the container and the input amount are different.

In this case, preferably, the image capturing unit performs image capturing on a bottom surface of the container, and the control unit acquires container bottom information including a height position of the bottom surface of the container based on focus position information of the image capturing unit with respect to the bottom surface of the container, and specifies the height position of the placement surface on the base from the position information and the container bottom information acquired by the image capturing.

With the biological subject treatment device, the container bottom information can also be acquired using the image capturing unit included in the biological subject treatment device.

In the biological subject treatment device, the biological subjects are preferably placed in the container in a mode of being in contact with the placement surface in an upper culture medium layer including a semi-solid culture medium stacked on the underlying culture medium layer.

With the biological subject treatment device, a state can be achieved in which the periphery of the biological subjects is surrounded by the underlying culture medium layer and the upper culture medium layer. Therefore, a state can be achieved in which the growth factor can be supplied from the entire periphery of the biological subjects.

In the biological subject treatment device, the biological subjects may be placed in the container in a mode of settling down on the placement surface in a culture medium injected on the underlying culture medium layer. Alternatively, an air layer may be provided above the underlying culture medium layer, and the biological subjects may be placed in the container in a mode of being in contact with the placement surface.

In the biological subject treatment device, desirably, the treatment unit is a head that is controlled by the control unit, the head including a suction tip attached at a lower end, and the head capable of being raised and lowered and being moved in a horizontal direction, the predetermined treatment is a treatment of sucking the biological subjects on the placement surface with the suction tip and transferring the biological subjects to a predetermined location, and the control unit lowers the head according to the treatment position at the first point, causes the suction tip to suck the biological subjects, and then raises the head, and lowers the head according to the used treatment position and causes the suction tip to suck the biological subjects at the second point.

With the biological subject treatment device, the biological subjects can be sucked into the suction tip even at the second point by using information on the treatment position used at the first point. Therefore, the efficiency of the suction operation and the transfer operation of the biological subjects can be improved.

According to the present disclosure described above, the efficiency of biological subject treatment can be improved in the biological subject treatment device that performs a predetermined treatment on the biological subjects placed in the container.

What is claimed is:
1. A biological subject treatment device comprising:
a base on which a container is mounted, the container being configured to accommodate an underlying culture medium layer including a semi-solid or solid culture medium, and a plurality of biological subjects placed at various places on a placement surface that is a flat upper surface of the underlying culture medium layer;
a treatment unit configured to perform a predetermined treatment on the plurality of biological subjects placed on the placement surface; and
a controller configured to control an operation of the treatment unit, such that the controller is configured to:
acquire position information including a height position of the placement surface;
specify a treatment position on each of the biological subjects existing at a first point on the placement surface based on the position information, and cause the treatment unit to perform the predetermined treatment according to the treatment position; and
then cause the treatment unit to perform the predetermined treatment on each of the biological subjects existing at a second point different from the first point on the placement surface by using the treatment position, wherein
the container and the underlying culture medium layer are formed of a translucent material,
the biological subject treatment device further comprises an image capturing unit configured to capture an image of the underlying culture medium layer accommodated in the container in a thickness direction of the underlying culture medium layer, and the controller is configured to acquire the position information based on focus position information of the image capturing unit with respect to the placement surface, and wherein the image capturing unit is configured to perform image capturing on a bottom surface of the container, and the controller is configured to acquire container bottom information including a height position of the bottom surface of the container based on focus position information of the image capturing unit with respect to the bottom surface of the container, and specify the height position of the placement surface on the base from the position information and the container bottom information acquired by the image capturing.

2. The biological subject treatment device according to claim 1, wherein the biological subjects are placed in the container in a mode of being in contact with the placement surface in an upper culture medium layer including a semi-solid culture medium stacked on the underlying culture medium layer.

3. The biological subject treatment device according to claim 1, wherein the biological subjects are placed in the container in a mode of settling down on the placement surface in a culture medium injected on the underlying culture medium layer.

4. The biological subject treatment device according to claim 1, wherein an air layer is provided above the underlying culture medium layer, and the biological subjects are placed in the container in a mode of being in contact with the placement surface.

5. The biological subject treatment device according to claim 1, wherein the treatment unit is a head that is controlled by the controller, the head including a suction tip attached at a lower end, and the head capable of being raised and lowered and being moved in a horizontal direction, the predetermined treatment is a treatment of sucking the biological subjects on the placement surface with the suction tip and transferring the biological subjects to a predetermined location, and the controller is configured to lower the head according to the treatment position at the first point, cause the suction tip to suck the biological subjects, and then raise the head, and lower the head according to a used treatment position and cause the suction tip to suck the biological subjects at the second point.

\* \* \* \* \*